(12) United States Patent
Willimann

(10) Patent No.: US 8,778,415 B2
(45) Date of Patent: Jul. 15, 2014

(54) ANTIMICROBIAL AND ANTIVIRAL COMPOSITION

(75) Inventor: John A. Willimann, Chevy Chase, MD (US)

(73) Assignee: Global Life Technologies Corp., Chevy Chase, MD (US)

( * ) Notice: Subject to any disclaimer, the term of this patent is extended or adjusted under 35 U.S.C. 154(b) by 212 days.

(21) Appl. No.: 13/447,912

(22) Filed: Apr. 16, 2012

(65) Prior Publication Data

US 2012/0225137 A1 Sep. 6, 2012

Related U.S. Application Data

(60) Continuation of application No. 12/658,116, filed on Feb. 1, 2010, now Pat. No. 8,158,163, which is a division of application No. 11/906,640, filed on Oct. 3, 2007, now abandoned, which is a continuation-in-part of application No. 11/189,242, filed on Jul. 26, 2005, now abandoned.

(51) Int. Cl.
*A01N 65/00* (2009.01)

(52) U.S. Cl.
USPC ........................................... 424/725

(58) Field of Classification Search
None
See application file for complete search history.

(56) References Cited

FOREIGN PATENT DOCUMENTS

JP     02006248908 A  *  9/2006

* cited by examiner

*Primary Examiner* — Michael Meller
(74) *Attorney, Agent, or Firm* — Robert M. Downey, P.A.

(57) ABSTRACT

An antimicrobial and antiviral barrier composition for topical application to the proximal anterior nares incluides an antiseptic solution in combination with one or more *citrus* oils such as, for example, *citrus sinensis* (orange oil). Various embodiments may also include one or more of the following additional ingredients: lauric acid; d-limonene; soy oil; emu oil; grapefruit seed extract; *glycine soja; simmondsia chimensis* (Jojoba); *aloe vera*; and a preservative, such as sodium benzoate, BHT, benzalkonium chloride, vitamin E.

4 Claims, No Drawings

ANTIMICROBIAL AND ANTIVIRAL COMPOSITION

BACKGROUND OF THE INVENTION

This patent application is a continuation patent application of patent application Ser. No. 12/658,116 filed on Feb. 1, 2010, which is a divisional of patent application Ser. No. 11/906,640 filed on Oct. 3, 2007, now abandoned, which is a Continuation-In-Part (CIP) patent application of patent application Ser. No. 11/189,242 filed on Jul. 26, 2005, now abandoned.

Field of the Invention

This invention relates to antiseptic compositions and, more particularly, to a nasal antiseptic barrier composition having antimicrobial, antiviral, and antifungal properties.

Discussion of the Related Art

In recent years, outbreaks of new and potentially deadly diseases such as Severe Acute Respiratory Syndrome (SARS) and the Avian Influenza have captured worldwide attention and concern. New and unusual strains of the flu virus have also emerged in the last few years and have spread throughout the world population at epidemic levels. It is believed that increases in world population, rapid travel between distance regions and high concentration of individuals in confined areas where there is poor air filtration (e.g. aircraft, trains, buses and tourist sites) have resulted in the increase in the number of, as well as mutation of, pathogenic organisms.

The onset of respiratory disease is primarily a result of inhalation of airborne pathogens through the nose and mouth. However, the oral cavity is better equipped to kill airborne pathogens before they can enter and infect the body. Specifically, saliva in the mouth captures many airborne pathogens before they are inhaled into the lungs. Once the saliva containing the pathogens is swallowed, stomach acids are highly effective in killing these pathogens before they can infect the body. The nasal passages, on the other hand, are less effective in trapping and killing microorganisms. Airborne pathogens inhaled through the nose usually enter the lungs where there can cause respiratory infection or other types of infection once these pathogens enter the blood stream.

Worldwide concern of epidemic outbreaks has lead to more drastic preventative measures including emergency mass production of new vaccines. Individuals have adopted preventive practices such as frequent hand washing and use of antiseptic hand lotions and wipes. While these are good practices to help reduce the possibility of infection, they are not long lasting and are usually only effective to kill germs that were on the hands or other areas of the body prior to cleansing. With little to no residual effect, the hands can become contaminated with pathogens shortly after washing.

Some societies have begun to use face masks as a means of protection against respiratory infections. Face masks are effective to prevent entry of pathogens into the respiratory system. However, the use of face masks is generally impractical, inefficient and socially unappealing.

Besides the concern for the health and well beings of individuals there are economic interests in preventing the spread on communicable diseases. For instance, over the course of just one year Americans suffer approximately 1 billion colds. The economic impact of the common cold is enormous. The National Center for Health Statistics (NCHS) estimates that over 70 million cases of the common cold in the United States required medical attention or resulted in restricted activities. Colds cause more than 50 million days of restricted activity and 25 million days lost from school and the work place. Overall, the estimated cost to the U.S. economy of the common cold and other related illnesses is approximately $150 billion per year.

Accordingly, there is an immediate need for more effective protection measures to decrease the spread of disease, and particularly respiratory infections that result from exposure to airborne pathogens.

SUMMARY OF THE INVENTION

The present invention is directed to an antimicrobial and antifungal barrier composition for topical application to the proximal anterior nares (rim surrounding the nostrils). The composition includes an antiseptic solution in combination with *cocos nucifera* (coconut oil) and one or more *citrus* oils such as, for example, *citrus sinensis* (orange oil). Examples of an antiseptic solution include one or more alcohols, such as ethyl alcohol, or hydrogen peroxide. The composition may include one or more additional ingredients, including: lauric acid; *simmondsia chinensis* (Jojoba); d-limonene; soy oil; emu oil; grapefruit seed extract; *glycine soja; aloe vera* and a preservative, such as sodium benzoate, benzalkonium chloride, BHT and vitamin E.

When properly applied to the skin surrounding the nostril openings, the composition has been proven effective in killing 99.99999% (7 log) or greater germs. This extremely efficient antimicrobial efficiency persists for at least 8 hours. Results from laboratory studies have shown efficacy in killing *streptococcus* (*pneumoniae* and *pyogenes*), *staphylococcus aureus, mycobacterium smegmatis*, and *haemophilus* influenza bacterias. The antimicrobial and antiviral composition of the present invention was further shown to be effective in eradicating the rhinovirus and influenza A virus (avian flu), as well as the corona virus. The corona virus is known to be the cause of SARS.

In addition to the anti-pathogen properties, the composition of the present invention has also been proven to help alleviate the body's immuno-response to many allergens including, but not limited to, dust mites, pollen, hay fever, animal dander, dust, particulate pollution, ozone, sulfur dioxide, and nitrogen oxide. The composition is effective in trapping these allergens and alleviating the body's response to their presence. In the case of ozone, SO2 and NO, the composition acts as a barrier in the nose and lessens the IGA response in the body. It is also believed that the composition works to lessen the Interleukin expression in the nose, especially ILB, commonly perspective for the inflammation response in the nasal cavity. A particularly effective formulation includes one or more of the following ingredients in combination with *citrus* oils, *cocos nucifera* and *glycine soja*: beeswax; bees milk; and fruit wax.

Objects and Advantages of the Invention

Considering the forgoing, it is a primary object of the present invention to provide an antimicrobial and antiviral composition for topical application to the anterior nostril openings for protecting against harmful exposure to airborne pathogens.

It is a further object of the present invention to provide a safe and highly effective antimicrobial and antiviral composition for topical application to the rim of each nostril to provide protection against a broad spectrum of harmful pathogens for at least 8 hours.

It is still a further object of the present invention to provide an antimicrobial and antiviral composition for topical application to the rim of each nostril to enhance the natural filtration properties of the nose.

It is yet a further object of the present invention to provide an antimicrobial and antiviral composition for topical application to the rim of the nostrils for trapping and killing airborne pathogens before these pathogens can replicate within the nasal cavity.

It is still a further object of the present invention to provide an antimicrobial and antiviral composition that significantly reduces the number of harmful pathogens that proliferate freely within the nasal cavity, thereby minimizing the degree and severity of potential respiratory infection.

It is still a further object of the present invention to provide an antimicrobial and antiviral composition of topical application to the rim of the nostrils, and wherein the composition has a pleasant scent and contributes to the lubrication and filtration of the nasal passages.

It is yet a further object of the present invention to provide an antimicrobial and antiviral composition for topical application to the rim of the nostrils, wherein the composition is effective in trapping allergens and alleviating the body's response to their presence.

These and other objects of the present invention are more readily apparent with reference to the detailed description which follows.

DETAILED DESCRIPTION OF THE PREFERRED EMBODIMENTS

The present invention is directed to a long lasting antimicrobial and antiviral barrier composition for topical application to the proximal anterior nares (skin surface surrounding the opening of the nostrils). The antimicrobial and antiviral composition of the present invention incorporates the use of one or more antiseptic solutions in combination with *cocos nucifera* (coconut oil), *citrus sinensis* (orange oil), and *simmondsia chinensis* (Jojoba). In one preferred embodiment, the antiseptic solution is USP ethyl alcohol. In another preferred embodiment, the antiseptic solution is hydrogen peroxide. Other alcohols and antiseptic agents are contemplated for use in the composition as the antiseptic solution, either alone or as a combination.

The essential ingredients of the composition are present according to the following percentages by weight of the composition:

| Additional Ingredients | Amount (% by Weight of the Composition) |
| --- | --- |
| Antiseptic solution | between 5% and 75% |
| *Citrus Sinensis* | between 0.05% and 60% |

The antimicrobial and antiviral composition of the present invention may further include the following additional ingredients, alone or in combination: lauric acid; *simmondsia chinensis*; d-limonene; soy oil; emu oil; grapefruit seed extract; *glycine soja*; and a preservative such as sodium benzoate, benzalkonium chloride, BHT, vitamin E. These additional ingredients of the composition may be present according to the following percentages by weight of the composition:

| Additional Ingredients | Amount (% by Weight of the Composition) |
| --- | --- |
| Lauric acid | between 0.01% and 5% |
| *Simmondsia Chinensis* | between 0.1% and 75% |
| D-limonene | between 0.01% and 5% |
| *Glycine Soja* (soy oil) | between 0.1% and 80% |

| Additional Ingredients | Amount (% by Weight of the Composition) |
| --- | --- |
| Emu oil | between 0.1% and 10% |
| Grapefruit Seed extract | between 0.1% and 8% |
| *Aloe Vera* | between 0.1% and 30% |
| Benzalkonium Chloride | between 0.05% and 0.15% |
| BHT | between 0.05% and 2% |
| Vitamin E | between 0.1% and 4% |
| *Cocos Nucifera* | between 0.025% and 70% |

A further embodiment of the composition has been proven to help alleviate the body's immune-response to many allergens and pollutants. The following ingredients have been found to be effective in the composition when present according to the following percentages by weight of the composition:

| Ingredients | Amount (% by Weight of the Composition) |
| --- | --- |
| Beeswax | between 0.01% and 30% |
| Bees Milk | between 0.01% and 30% |
| Fruit Wax | between 0.1% and 5% |

Antiseptic solutions such as ethyl alcohol and hydrogen peroxide typically evaporate at a rapid rate. For this reason, when antiseptic solutions are used alone, they usually have little to no residual effect. The base oils of the composition, namely *citrus sinensis, cocos nucifera*, and *simmondsia chinensis*, are effective to trap the antiseptic solution in a pseudo-emulsion antiseptic that remains active for an extended period of time. This allows the composition to have a long lasting antimicrobial and antiviral protection. The base oils also provide antimicrobial, antiviral and antifungal properties.

When the base oils are combined with the antiseptic solution, a synergistic effect is observed. For instance, the efficacy of any one of the base oils or the antiseptic solution, alone, does not exceed 99.99% (4 log). However, when all ingredients are combined in suitable ratios an unexpected removal efficiency rating (efficacy) of 99.99999% (7 log) or greater is achieved. This synergism is a key to the novelty of the composition, providing antimicrobial and antiviral kill levels that are significantly greater than those observed in connection with any of the ingredients individually or other known antimicrobials and antivirals.

The following examples demonstrate various combinations of ingredients, including the 3 essential ingredients, which have been observed to yield antimicrobial and antiviral kill rates of 7 log or greater.

EXAMPLE 1

| Ingredient | Amount (% by Weight of the Composition) |
| --- | --- |
| USP Ethyl Alcohol (190 proof) | 24.9% |
| *Cocos Nucifera* | 3% |
| *Citrus Sinensis* | 2% |
| *Glycine Soja* | 70% |
| Sodium Benzoate (preservative) | 0.1% |

EXAMPLE 2

| Ingredient | Amount (% by Weight of the Composition) |
| --- | --- |
| USP Ethyl Alcohol (190 proof) | 34.8% |
| Cocos Nucifera | 3% |
| Citrus Sinensis | 2% |
| Aloe Vera | 3% |
| Lauric Acid | 0.1% |
| Glycine Soja | 57% |
| Sodium Benzoate (preservative) | 0.1% |

EXAMPLE 3

| Ingredient | Amount (% by Weight of the Composition) |
| --- | --- |
| USP Ethyl Alcohol (190 proof) | 54.8% |
| Cocos Nucifera | 10% |
| Citrus Sinensis | 5% |
| Aloe Vera | 30% |
| Lauric Acid | 0.1% |
| Glycine Soja | 0.1% |

EXAMPLE 4

| Ingredient | Amount (% by Weight of the Composition) |
| --- | --- |
| USP Ethyl Alcohol (190 proof) | 24.9% |
| Cocos Nucifera | 8% |
| Citrus Sinensis | 8% |
| Aloe Vera | 29.45% |
| Lauric Acid | 0.2% |
| Glycine Soja | 29.45% |

EXAMPLE 5

| Ingredient | Amount (% by Weight of the Composition) |
| --- | --- |
| USP Ethyl Alcohol (190 proof) | 24.9% |
| Emu Oil | 3% |
| Citrus Sinensis | 2% |
| Glycine Soja | 70% |
| Sodium Benzoate (preservative) | 0.1% |

EXAMPLE 6

| Ingredient | Amount (% by Weight of the Composition) |
| --- | --- |
| Glycine Soja | 35% |
| Citrus Sinensis | 30% |
| Cocos Nucifera | 30% |
| Bees Milk | 4.9% |
| Preservative | 0.1% |

* FOR ALLERGENS AND POLLUTANTS

EXAMPLE 7

| Ingredient | Amount (% by Weight of the Composition) |
| --- | --- |
| Bees Milk | 50% |
| Lecithin | 10% |
| Citrus Sinensis | 20% |
| Glycine Soja | 19.9% |
| Preservative | 0.1% |

* FOR ALLERGENS AND POLLUTANTS

EXAMPLE 8

| Ingredient | Amount (% by Weight of the Composition) |
| --- | --- |
| USP Ethyl Alcohol (190 proof) | 50% |
| Cocos Nucifera | 3% |
| Citrus Sinensis | 2% |
| Simmondsia chinensis | 35% |
| Glycine Soja | 9.5% |
| Sodium Benzoate (preservative) | 0.1% |
| BHT (preservative) | 0.1% |
| Benzalkonium chloride | 0.1% |
| Vitamin E | 0.2% |

EXAMPLE 9

| Ingredient | Amount (% by Weight of the Composition) |
| --- | --- |
| USP Ethyl Alcohol (190 proof) | 50% |
| Cocos Nucifera | 3% |
| Citrus Sinensis | 2% |
| Simmondsia chinensis | 40% |
| Glycine Soja | 4.6% |
| BHT (preservative) | 0.1% |
| Benzalkonium chloride | 0.1% |
| Vitamin E | 0.2% |

EXAMPLE 10

| Ingredient | Amount (% by Weight of the Composition) |
| --- | --- |
| USP Ethyl Alcohol (190 proof) | 50% |
| Cocos Nucifera | 2% |
| Citrus Sinensis | 15% |
| Simmondsia chinensis | 30% |
| Glycine Soja | 2.5% |
| BHT (preservative) | 0.1% |
| Benzalkonium chloride | 0.1% |
| Vitamin E | 0.3% |

In use, the antimicrobial and antiviral composition is applied to the skin surface surrounding the opening of the nostrils according to the following instructions:

1). Shake the bottle (containing the composition) well to insure complete mixture of the ingredients.

2) Apply approximately 4 drops of the composition to the cotton tip of a cotton swab so that the cotton tip is fully saturated with the composition.

3). Place the thumb and index finger on the swab stem directly below the wetted cotton tip of the swab. Prepare to apply the composition to the rim of each nostril just past the nasal opening. Caution: Do not extend the swab into the nasal canal any further than the short length of the cotton tip of the swab (about 1 cm or 3.8'). The swab stem should never enter the nose.

4). Carefully place only the cotton tip of the swab just inside of the nostril opening. Using a gentle motion, make 3 or 4 circles to fully apply the composition to the rim of the nostril. Repeat this step for the other nostril.

5). Discard the swab. Gently squeeze the nostrils together to ensure even distribution of the solution about the rim surrounding each nostril opening.

In order to evaluate the antimicrobial efficacy of one sample of the composition when applied to the proximal external nares of human volunteers, the test study was conducted at Bioscience Laboratory, Inc. in Bozeman, Mont. The results of the study are set forth below.

Purpose of Study:

This study was designed to evaluate the persistent antimicrobial efficacy of one (1) test product intended for prevention of airborne illness when applied within the proximal nares (the first 0.25" of a naris) and one (1) control material.

Scope of Study:

Thirty (30) human subjects were evaluated in this study. Twenty-five (25) human subjects were used to evaluate the test product, and five (5) human subjects were used to evaluate the control material (sterile deionized water). Samples were taken from the proximal nares (the first 0.25" of the nostrilar canal). Baseline samples were collected a minimum of twenty-four (24) hours apart to allow recolonization of the normal flora. On the test day, the product was applied to each naris. Each naris was apportioned on a sagittal plane into two (2) sample sites, medial and lateral. Ten (10) samples each were taken for the two (2) hour±fifteen (15) minutes and four (4) hour±fifteen (15) minutes post-product exposures to the test product, and for the immediate (within one [1] minute of application) and four (4) hour±fifteen (15) minutes post-product exposures to the control material. Twenty (20) samples each were taken for the immediate (within one [1] minute of application), six (6) hour±fifteen (15) minutes, eight (8) hour±fifteen (15) minutes, and twelve (12) hour±fifteen (15) minutes post-product exposures to the test product.

Validation of the Neutralizer System:

A neutralization study was performed to assure the effectiveness of the neutralizers used in the diluting medium. The neutralization followed guidelines set forth in ASTM E 1054-02, *Standard Test Methods for Evaluation of Inactivators of Antimicrobial Agents*, except that the microorganism was added to the neutralizers prior to the addition of the test or comparison antiseptic. *Staphylococcus aureus* (ATCC #6538) was used as the challenge species in the neutralizer validation study. The neutralization study demonstrated that the antimicrobial activities of the test and reference products were effectively eliminated.

Adverse Events:

No Adverse Events were observed during or following completion of this study.

Results:

Table I presents the statistical summary of the log 10 recovery values with relation to use of the Test Product.

TABLE I

Statistical Summary of the log 10 Recovery Values for the Test Product

| Sample | Sample Size | Mean | Standard Deviation | 95% Confidence Interval | $Log_{10}$ Reduction |
|---|---|---|---|---|---|
| Baseline Pooled | 25 | 4.51 | 0.39 | 4.35 to 4.67 | N/A |
| Immediate Post-Product Exposure | 21 | 3.38 | 1.28 | 2.79 to 3.96 | 1.13 |
| 2 Hours Post-Product Exposure | 11 | 3.61 | 1.14 | 2.85 to 4.38 | 0.90 |
| 4 Hours Post-Product Exposure | 9 | 3.58 | 0.56 | 3.15 to 4.02 | 0.93 |
| 6 Hours Post-Product Exposure | 18 | 3.59 | 0.52 | 3.34 to 3.85 | 0.92 |
| 8 Hours Post-Product Exposure | 21 | 3.88 | 0.65 | 3.58 to 4.17 | 0.63 |
| 12 Hours Post-Product Exposure | 19 | 4.28 | 0.67 | 3.96 to 4.60 | 0.23 |

Table II presents the Statistical Summary of the log 10 recovery values with relation to use of the Control Material (Sterile Deionized Water)

TABLE II

Statistical Summary of the log 10 Recovery Values for the Control Material Sterile Deionized Water

| Sample | Sample Size | Mean | Standard Deviation | 95% Confidence Interval | $Log_{10}$ Reduction |
|---|---|---|---|---|---|
| Baseline Pooled | 5 | 4.31 | 0.49 | 3.70 to 4.92 | N/A |
| Immediate Post-Product Exposure | 10 | 4.66 | 0.59 | 4.24 to 5.08 | 0.00 |
| 4 Hours Post-Product Exposure | 10 | 4.23 | 0.63 | 3.78 to 4.68 | 0.08 |

While the composition of the present invention has been described and exemplified according to several preferred embodiments thereof, it is recognized that departures from the instant disclosure are fully contemplated within the spirit and scope of the invention which is not to be limited except as defined in the following claims as interpreted under the Doctrine of Equivalents.

What is claimed is:

1. An antimicrobial, antiviral and antifungal composition consisting essentially of:
   ethanol in an amount of between 5.0% and 75.0% by weight of the total composition, orange oil in an amount of between 0.05% and 60.0% by weight of the total composition, jojoba oil in an amount of between 0.1% and 75% by weight of the total composition and vitamin E in an amount of between 0.1% and 4.0% by weight of the total composition.

2. An antimicrobial, antiviral and antifungal composition consisting essentially of:
   ethanol in an amount of between 5.0% and 75.0% by weight of the total composition, orange oil in an amount of between 0.05% and 60.0% by weight of the total composition, benzalkonium chloride in an amount of between 0.05% and 0.15% by weight of the total composition, jojoba oil in an amount of between 0.1% and 75% by weight of the total composition and vitamin E in an amount of between 0.1% and 4.0% by weight of the total composition.

3. An antimicrobial, antiviral and antifungal composition consisting essentially of:
ethanol in an amount of between 5.0% and 75.0% by weight of the total composition, orange oil in an amount of between 0.05% and 60.0% by weight of the total composition, coconut oil in an amount of between 0.025% and 70% by weight of the total composition, jojoba oil in an amount of between 0.1% and 75% by weight of the total composition and vitamin E in an amount of between 0.1% and 4.0% by weight of the total composition.

4. An antimicrobial, antiviral and antifungal composition consisting essentially of:
ethanol. in an amount of between 5.0% and 75.0% by weight of the total composition, orange oil in an amount of between 0.05% and 60.0% by weight of the total composition, lauric acid in an amount of between 0.01% and 5.0% by weight of the total composition, jojoba oil in an amount of between 0.1% and 75% by weight of the total composition and vitamin E in an amount of between 0.1% and 4.0% by weight of the total composition.

* * * * *